United States Patent
Bucke et al.

(10) Patent No.: US 6,939,683 B2
(45) Date of Patent: Sep. 6, 2005

(54) SOLUTION ASSAY METHOD USING POLARIMETRY

(75) Inventors: Christopher Bucke, London (GB); Max Adlard, London (GB); Victoria Singleton, Huntingdon (GB); Jennifer Horn, Huntingdon (GB)

(73) Assignee: Optical Activity Limited, Huntingdon (GB)

( * ) Notice: Subject to any disclaimer, the term of this patent is extended or adjusted under 35 U.S.C. 154(b) by 325 days.

(21) Appl. No.: 09/995,737

(22) Filed: Nov. 29, 2001

(65) Prior Publication Data

US 2003/0100041 A1 May 29, 2003

(51) Int. Cl.⁷ .................................................. C12Q 1/54
(52) U.S. Cl. ............................................ 435/14; 435/4
(58) Field of Search .............................. 435/14, 4, 18, 435/103, 211; 127/46.1, 53

(56) References Cited

FOREIGN PATENT DOCUMENTS

| EP | 0 534 166 | | 8/1992 |
|---|---|---|---|
| EP | 0 534 166 A1 | * | 8/1992 |
| WO | WO 00/68695 | * | 11/2000 |

OTHER PUBLICATIONS

Oikawa S. Determination of Sucrose, Invert Sugar and Raffinose in Sugar Solutions. Seito Gijutsu Kenkyu Kaishi 1962, vol. 11, pp. 28–37.*

SU–B–734558 (Sugar Research Institute) (abstract only).

A New Polarimetric Dextran And Sucrose Test, by Christopher Bucke, Max Adlard, Victoria Singleton, and Jennifer Horn; Bharatiya Sugar Journal, Mar. 2001, pp. 127–134 (correction on named authors was corrected in later edition of the Journal).

A New Polarimetric Method For The Analysis Of Dextran And Sucrose, by Victoria Singleton, Jennifer Horn, Christopher Bucke, and Max Adlard; International Sugar Journal, vol. 103, No. 1230, Jun. 2001; pp. 251–254.

A New Polarimetric Method For The Analysis Of Dextran And Sucrose, by Victoria Singleton, Jennifer Horn, Christopher Bucke and Max Adlard; Proc. S.T.A.I. 63, pp. 110–119, 2001.

Double–Polarization Methods, Cane Sugar Handbook, 12th Edition, ed. Chen & Chou, J. Wilsy, 1993, pp. 831–842.

* cited by examiner

*Primary Examiner*—Ralph Gitomer
(74) *Attorney, Agent, or Firm*—Millen, White, Zelano & Branigan, P.C.

(57) ABSTRACT

A method for the measurement of the concentration of a material such as dextran or raffinose in a solution, notably a sugar solution, includes the steps of measurement of the optical rotation of a solution sample, treatment of the sample with a reactive agent, measurement of the optical rotation of the sample after treatment to ascertain the difference that said treatment has made, and calculation of the concentration of the material by reference of said difference to a suitable standard. The reactive agent reacts with the material sufficiently to alter the optical rotation of the sample.

11 Claims, 3 Drawing Sheets

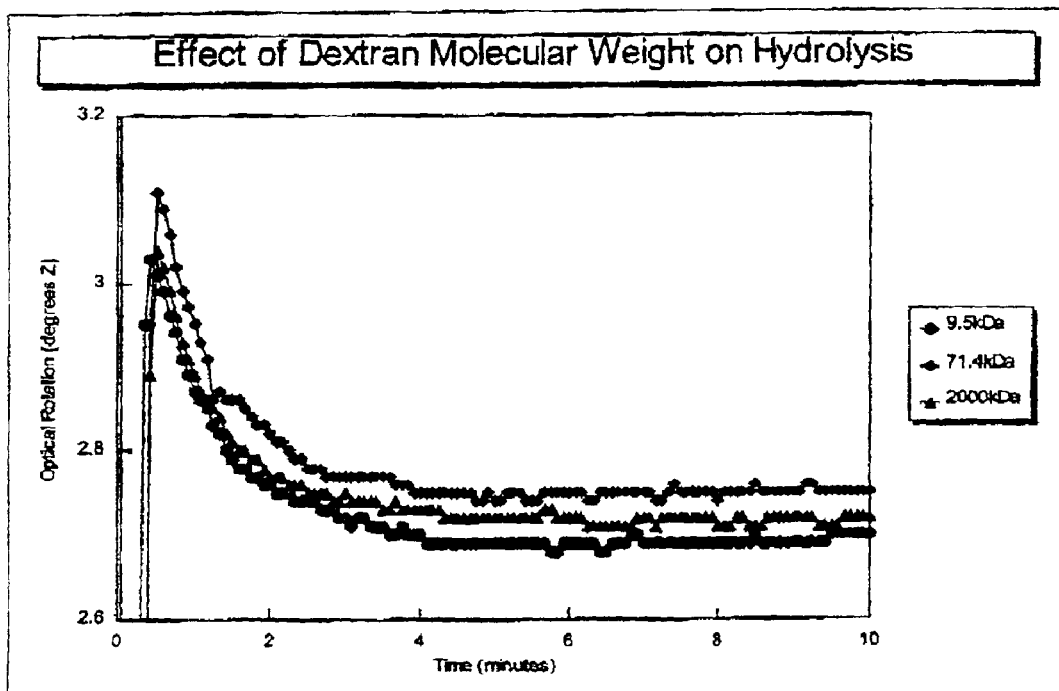
Fig. 1. Graph showing the progress over time of the hydrolysis of three different molecular weight dextrans as shown by the change in optical rotation.

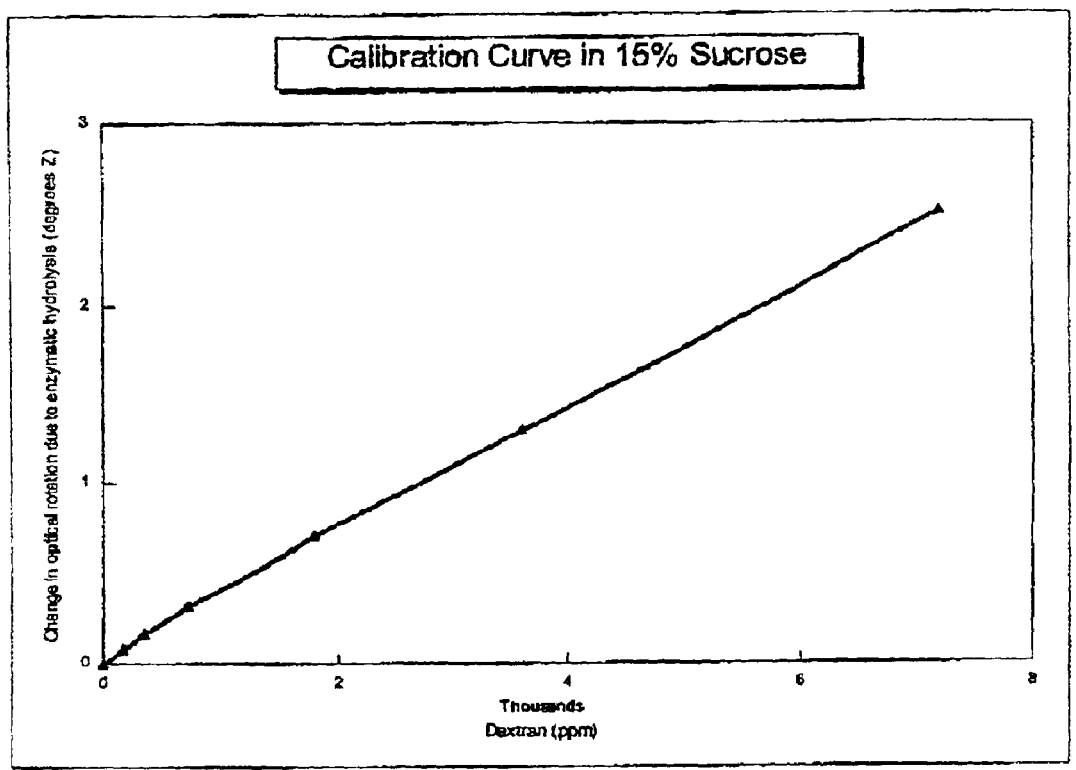
Fig. 2. Graph showing the relationship between dextran concentration and change in optical rotation due to hydrolysis by dextranase.

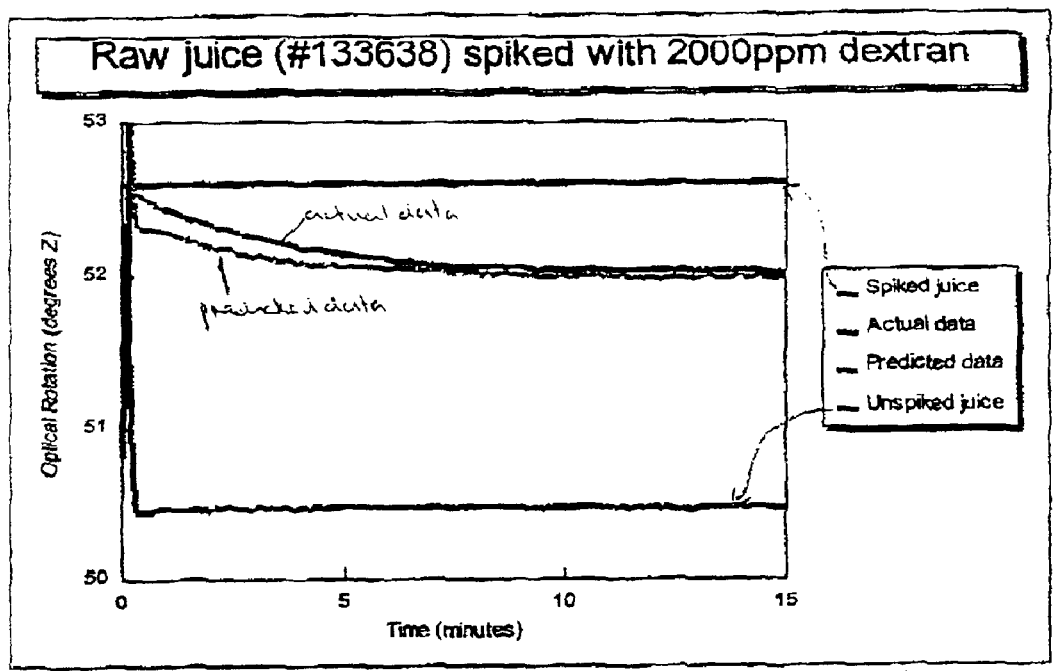
Fig. 3. Graph showing the difference between the rotational values of the clean and spiked juice and then the actual data compared to the predicted data the latter of which arises from adding the data of the reaction in water to that of the unspiked juice (after accounting for controls).

SOLUTION ASSAY METHOD USING POLARIMETRY

The present invention relates to a method for the determination of the concentration of a material in solution.

In particular, the present invention relates to the use of polarimetry. Polarimetry is the study of the rotation of plane polarised light as light passes through a material. Compounds which are able to rotate the plane of plane polarised light are known as optically active compounds.

Polarimetry is widely used for the analysis of carbohydrates, such as sucrose, and is commercially used in the sugar cane industry in this regard to measure the quantity of sucrose in crude sugar cane juice. The degree of optical rotation of a given cane juice sample is taken as a measure of the quantity of sucrose that is present.

If a solution containing an analyte of interest, such as sucrose, is contaminated with another optically active compound, polarimetry may provide a misleading result. This is because polarimetry measures the overall rotation of a solution, irrespective of the specific components which produce the optical rotation. In the sugar cane industry, for example, raw cane juice may be contaminated with the polysaccharide dextran. This contamination provides a two fold problem.

First, high molecular weight dextran increases solution viscosity and inhibits sucrose crystallisation, thus slowing the sugar refining process. Specifically, dextran in the juice leads to "gumming" of the factory machinery and formation of a layer which blocks filter cloths used in the refining. The effect low molecular weight dextran has on the crystallisation process can be dramatic by preventing lateral extension. The insolubility of dextran in alcohol renders sugars containing dextran unsuitable for the production of alcoholic beverages. Accordingly penalties may be charged to cane sugar suppliers if the content of dextran in raw sugar exceeds, for example, 250 part per million.

Secondly, the dextran molecule is highly dextro-rotatory, having a specific optical rotation approximately three times greater than that of sucrose. Thus, if polarimetry is used to determine the concentration of sucrose in a dextran-contaminated sample, false readings for the concentration of sucrose are obtained, due to the contribution of dextran to the overall optical rotation of the sample. Specifically, polarimetric readings are obtained which overestimate the sucrose content of the cane juice and result in over payment to the farmer for cane which will continue to be problematic throughout processing. Contamination with any other optically active material also produces false readings.

In the sugar beet industry, contamination by ramose and raffinose family of oligosaccharides (such as stachyose and verbascose) also presents problems in sugar production. Raffinose also leads to the overestimation of sucrose concentration in beet samples. Moreover, raffinose interferes with the crystallisation process in a similar manner to dextran, slowing crystal growth by inhibiting crystal growth along one face. This results in deformed crystals which are harvested snore slowly than normal crystals.

Accordingly, there is a requirement to measure accurately the concentration of contaminants in sugar samples, such as dextran in cane and beet samples and raffinose in beet samples. Knowledge of the concentration of a contaminant such as dextran, for example, allows the exact concentration of sucrose to be more accurately determined.

The current method to measure dextran concentration involves removal of protein from the cane juice by treatment with trichloroacetic acid, a-amylase to remove starch and lead sub-acetate to remove any colour which might interfere with the assay, followed by addition of ethanol to the clarified juice. This produces a "haze" which is measured by its turbidity, and taken to be dextran. The method is called the CSR Haze Test, and is the only technique to have been given status by ICUMSA (International Commission for Uniform Methods of Sugar Analysis), although it was later withdrawn due to its shortcomings. Specifically the CSR Haze Test is not capable of detecting low molecular weight dextran, and false readings are also obtained if the sample contains other polysaccharides. Moreover the use of lead-subacetate is undesirable on environmental and health grounds.

Alternative methods involving the use of antibodies to detect dextran are available, but have a disadvantage of being relatively expensive, complicated and slow.

There is, therefore, still the need for an accurate, safe and cheap method for the analysis of the concentration of optically active materials in solution.

The present invention set out to address this need.

In the first aspect, the present invention provides a method for the measurement of the concentration of a material in a solution, the method comprising the steps of:
1 measurement of the optical rotation of a solution sample;
2 treatment of the sample with a reactive agent, reactive with the material, sufficient to alter the optical rotation of the sample;
3 measurement of the optical rotation of the sample after treatment; and
4 calculation of the concentration of the material by reference to a suitable standard.

We have now discovered that the concentration of an optically active material may be examined by polarimetry, in combination with targeted modification of the optically active material. For example, in a natural cane sugar solution or beet sugar containing dextran, the enzyme dextranase may be used to break down the dextran component in the sample. Dextran breakdown in this way results in a change in optical rotation of the sample, as the dextran breakdown products have different optical activity to dextran. This reaction is rapid when the enzyme is in excess and thus the change in rotation between the original sample and that observed at a predetermined time after adding the dextranase can be calibrated to the original concentration of dextran present in the sample.

The method of the invention is not only applicable to identification of the concentration of any suitable optically active material, but also to non-optically active materials which have optically active derivatives, for example. In addition, the method is applicable to the measurement of concentration of materials, such as enzymes, which can alter the optically activity of a sample by converting a substrate to a product, wherein the optical activity of product and substrate are different. In this way the change in optical activity is used as an indicator of enzyme concentration. However, analysis of materials which are optically active is generally preferred.

Therefore, the invention preferably relates to a method for the measurement of the concentration of an optically active material in a solution, the method comprising the steps of:
1 measurement of the optical rotation of a solution sample;
2 treatment of the sample with a reactive agent, reactive with the optically active material, sufficient to alter the contribution of the optically active material to the optical rotation of the sample;
3 measurement of the optical rotation of the sample after treatment; and 4 calculation of the concentration of the optically active material by reference to a suitable standard.

Preferably the concentration of the material is assessed in a mixture of that material with other compounds, such as optically active compounds.

Suitably, the invention relates to measurement of the concentration of an optically active material within a sugar solution, such as a naturally occurring sugar solution, preferably a raw cane sugar or beet sugar solution. Preferably, the optically active material measured by the present invention is dextran, raffinose or one of the raffinose family of oligosaccharides such as stachyose and verbascose. Where raffinose is referred to herein, the invention also extends to these other raffinose family members, where appropriate. The optically active material measured by the present invention is most preferably dextrin in a sucrose syrup. In particular the optically active material is a contaminant of the solution.

Preferably the material can be broken down, substituted, modified or otherwise treated, such that the product of the treatment has a measurably different degree of optical rotation to the starting material. In this way, the treatment is sufficient to alter the contribution of the material to the optical rotation of the sample, and allows polarimetric analysis. Materials suitable for analysis in the present invention suitably have enzymatic breakdown products, modification products, or form adducts or other derivatives which have optical activity significantly different from the starting material, to allow for optimum technique sensitivity. However, even small changes in optical activity between products may be useful, depending upon the sensitivity of analysis required.

Treatment of the optically active material in a sample can be by any suitable physical or chemical means reactive with the material to alter its contribution to the overall optical activity of the sample, preferably selectively reactive. Preferably the treatment comprises breakdown of the material by enzymatic treatment or chemical modification. Preferably, the treatment specifically affects only the material of interest. Where the agent for treatment is an enzyme, we prefer that the enzyme is added to excess. We also prefer that the enzyme is substantially pure, such that it does not cause any unwanted side reactions. In analysis of cane sugar and beet sugar samples, for example, any dextranase used in the invention should be free from invertase contamination, to avoid unwanted sucrose breakdown.

Preferably the reactive agent for analysis of dextran concentration is dextranase. Preferably, the dextranase is obtained from Amano Enzyme Inc., or is of at least the same purity and specific activity as this product, having at least an activity of 30,000 units/ml, one unit being the amount of enzyme which produces reducing sugar corresponding to the reducing power of one micromole of sodium thiosulphate in one minute at 37° C. In the analysis of beet sugar, the reactive agent suitable for use in determining the concentration of raffinose is α-galactosidase.

Accordingly, in a preferred aspect, the present invention relates to a method for measuring the concentration of dextran in sugar cane juice, comprising the steps of;

1 Measuring the optical rotation of a cane sugar sample;
2 Treating the sample with dextranase;
3 Measuring optical rotation of the sample after treatment; and
4 Calculating the concentration of dextran by reference to a suitable standard curve.

Dextrans are polymers of D-glucopyranose (glucans) with predominantly α-(1–6) glucosidic linkages, which are commonly formed by the action of dextransucrase from *Leuconostoc mesenteroides* commercially, and *L. dextranicum* on sucrose. The structure and properties of the dextrans vary widely depending on the source organisms and environmental factors such as sucrose concentration, pH, temperature and aeration [Imrie F. K. E. and Tilbury R. H. (1972), Sugar Technol. Rev., 1 291–361.]. The branches are generally in the form of α-(1–3) and α-(1–4) linkages. Dextrans are insoluble in ethanol and aqueous solubility decreases as the proportion of non α-(1–6) linkages increases. It is the soluble dextrans which cause concerns in the sugar refinery, and to which the present invention generally refers.

Reaction of a reactive agent such as an enzyme with an optically active compound may produce another optically active compound. For example, the action of dextranase upon dextran ultimately produces a mixture of isomaltose and isomaltotriose, which may be further broken down to glucose. This allows the sensitivity of the assay to be modulated if necessary. Therefore, the present invention also include methods with more than one treatment step with a reactive agent, preferably more than one treatment step with an enzyme.

Preferably, the treatment of the material with the reactive agent occurs in solution, the agent being provided in a context of a solid support. The agent is suitably impregnated into paper, such as filter paper, although other suitable delivery means are available, such as cotton wool and resins such as ion exchange resins. Suitably, the agent is releasable from the solid support in solution, such that it can react with the material. Alternatively, the agent is active in the context of the solid support without the need to be released from it.

Accordingly, the present invention additionally provides a reactive agent in the context of a solid support, reactive with a material of interest, for use in the present invention. Preferably, the agent is an enzyme such as dextranase or α-galactosidase. Preferably, the solid support is filter paper or an ion exchange column. Most preferably the invention relates to a solid support, such as filter paper, comprising dextranase or α-galactosidase for use in the present invention.

A solid support comprising an enzyme may be produced by contacting a suitable paper sample with a solution of the enzyme, followed by drying. In this way, enzyme strips are produced, which are suitable for direct use with polarimetric analysis. Preferably the enzyme is protected when drying by the use of protectants such glycerol, more preferably protectants which have no optical activity. Other suitable protectants are well known to the skilled person.

In order to obtain a value for the absolute concentration of a material, such as an optically active material, the change in optical rotation for the sample may be compared to a known standard curve. Suitable standards may be generated by the measurement of optical rotation of known concentrations of the material of interest, such as dextran, before and after treatment with a suitable reactive agent such as dextranase. In the case of dextrin measurement, we prefer that the standard is assessed by measurement of a known quantity of dextran in a 10–20% sucrose sample, preferably 15% sucrose sample, which generally represents the sucrose concentration found in natural cane sugar juices.

In the analysis of dextrin, for example, the sugar sample is suitably treated with dextranase for a defined period, such as 5–10 minutes, after which time optical rotation is measured. Preferably the measurement is taken when the reading is stable, i.e. remains within +/−0.1° Z over a 10–20 second period, preferably a 15 second period. Standards are then prepared using measurements after equivalent treatment times.

The method of the present invention is highly accurate. A known quantity of dextran was added to fresh sugar cane samples, dextrin free, and then treated with dextranase. The changes in optical rotation of such samples was almost exactly the same as the change that occurred on treating a pure dextran solution of the same concentration with dextranase. Accordingly, the other components of the sugar cane samples do not affect assay viability. Thus, the present invention allows an accurate and sensitive detection of the quantity of an optically active material such as dextrin, in a sample, which comprises other optical active agents. Moreover, and surprisingly, although dextrin itself is a polymeric material of widely varying molecular weight, we have determined that the method of the present invention is significantly not affected by the molecular weight of the dextrin component.

We have found that the method of the present invention, when applied to dextran analysis, is sensitive enough to detect concentration of dextran as low as 200 parts per million in a sugar juice sample. This level of sensitivity is preferred and commercially important, as greater concentrations of dextran will result in cane suppliers being charged a penalty. Preferably, the invention is carried out using a SacchAAr 880 polarimeter [manufactured by Optical Activity Ltd.], at an infrared wavelength which allows detection at a suitable sensitivity. Note that analysis at IR wavelengths is important in the invention, as the solution colour interferes with readings at other wavelengths.

In the analysis of dextran concentration, we prefer that the sugar cane or beet solutions '1 are preferably treated with Celite for sample purification prior to polarimetry analysis. We have, surprisingly, also determined that the grade of Celite is important for accurate polarimetric analysis. Preferably, the Celite used is Filter Cel E.[available from World Minerals U.K. limited, Yorkshire, U.K.]. This is a particularly fine grading of diatomaceous earth. Other suitable Celites are those of substantially equivalent or finer median particle size, preferably having a median particle size of less than 19.3 microns, such as Celite 500, Celite 507, Celite 505 and Celite 577. Accordingly, the invention also relates to the use of Filter Cel E grade Celite and functional equivalents in the treatment of cane sugar prior to polarimetric analysis.

In addition, the invention extends to the use of Celite in clarification of any solution to be measured by near IR polarimetery, preferably using Filter Cel E or equivalents mentioned above. Accordingly, the present invention relates to a method of polarimetric analysis of a sample at near IR wavelengths, wherein the sample is pretreated with Filter Cel E grade Celite, or equivalent, before optical activity is measured.

The present invention also relates to kits for the assay of materials in solution, such as optically active materials, suitably those found in sugar solutions, comprising at least an agent reactive with the optically active material. Suitably the kit additionally comprises standards, or components to generate standards. The kit also may comprise software for use with a polarimeter, to automate the change in optical rotation of a standard with concentration of the material of interest. Preferably the reactive agent is provided in the context of a solid support. This prevents inaccuracies that result from incorrect dilution, due to poor laboratory practices, for example. In the specific case of dextran measurement any such kit preferably comprises dextranase in the context of a solid support, such as filter paper, suitable for use directly in the polarimetry sample. In the case of sugar beet, suitable kits comprise α-galactosidase in the context of solid support, for the assay of raffinose contamination.

Where the material to be studied is a naturally occurring sample, it is preferred that the method of the present invention is independent of pH over the naturally occurring pH range of the sample. In the case of dextran measurement, we have found that the results obtained using dextranase are independent of pH over the pH range normally found in sugar cane samples, for example pH 4.7–5.7.

The present invention is hereby further described with reference to the following Figures and Examples, which are illustrative of the present invention, but not binding upon it, wherein:

FIG. 1 illustrates the progress over time of the hydrolysis of three different molecular weight dextrans as shown by the change in optical rotation;

FIG. 2 illustrates the relationship between dextran concentration and change in optical rotation due to hydrolysis by dextranase; and FIG. 3 illustrates the difference between the rotational values of clean and spiked juice and then the actual data compared to the predicted data the latter of which arises from adding the data of the reaction in water to that of the unspiked juice (after accounting for controls).

EXAMPLE 1

Effect of Molecular Weight

It was necessary to determine if the specific optical rotation of dextran samples varied with molecular weight and if the extent of the change of rotation on hydrolysis was influenced by molecular weight.

The following dextrans were used:

Dextrans:

–9,5 kDa Sigma Cat. No. (D-9260)

–71.4 kDa Sigma Cat. No. (D-3759)

–2,000 kDa Sigma Cat. No. (D-5376)

These samples were dried for 3 hours in an oven at 105° C. followed by 24 hours in a desiccator containing phosphorus pentoxide. Weights were recorded before and after drying in order to determine percentage moisture. Solutions (4000 ppm in distilled water) were prepared.

In this and other examples, the invention was carried out using a SacchAAr 880 polarimeter [manufactured by Optical Activity Ltd.], at the infrared wavelength 880 nm. The polarimeter sample tube [also manufactured by Optical Activity Ltd.] was an A2 4×200 mm, maintained at 20° C. using an Index Instruments Ltd thermocirculator. Amano produced the dextranase used; its rotation after diluting 1:5 in distilled water is 0.22° Z. In the present examples the enzyme was used at this dilution.

To determine the starting optical rotation 1 ml of distilled water was added to 19 ml of each solution and the rotations measured.

To determine the change in rotation produced by dextranase, 1 ml. of dextranase was added to 19 ml. of dextran solution which was injected into the sample tube and the optical rotation [OR] recorded every 5 seconds for ten minutes using a data collection programme.

Results are shown in table 1 and FIG. 1

TABLE 1

Shows the change in OR due to enzymatic hydrolysis for three different molecular weight dextrans.

| Mw of Dextran (Daltons) | OR°Z (after correction for moisture content) | ΔOR°Z due to hydrolysis |
|---|---|---|
| 9,500 | 3.57 | 1.08 |
| 71,400 | 3.56 | 1.11 |
| 2,000,000 | 3.74 | 1.18 |

FIG. 1. shows the progress over time of the hydrolysis of three different molecular∴weight dextrans as shown by the change in optical rotation.

Table 1 shows no significant pattern in the effect of molecular weight on both the original OR and the extent of change in OR due to enzymatic hydrolysis. It is clear that a possible effect of molecular weight on the hydrolysis behaviour is the time taken to reach completion, which is slightly longer with the larger dextrans (FIG. 1).

EXAMPLE 2

Checks for Possible Side-reactions or Reactions With Other Substances Present in Cane Juice Several enzymes are known to exhibit side reactions distinct from the actual intended reaction and to react with other substrates of a similar structure to the actual substrate.

Method: A 5% solution of the analyte of interest was made up in distilled water. The OR of 19 ml. diluted with 1 ml. of distilled water was read on the polarimeter. 1 ml of dextranase was added to 19 ml. of analyte solution and the OR observed for 20 mins. Little or no change in the reading over time other than that accounted for with the enzyme control indicates no reaction.

Results:

| | |
|---|---|
| Sucrose | No reaction |
| Pectin | No reaction |
| Xylan | No reaction |
| Dextrin | No reaction |

Conclusion: Although the above list is far from exhaustive, there are no apparent reactions with these substances, which form the majority of dissolved solids constituent in sugar samples.

EXAMPLE 3

Effect of Preparation Steps on the Dextran Concentration

Cane juice samples must be clarified by filtration. It was necessary to determine the extent to which the clarification process removed dextran.

The OR of a 2000 ppm solution of 188 kDa dextran (Sigma Cat. No. D-4876) in distilled water was determined in the polarimeter. Celite Filter Cel E (2 g) was added to 100 ml of the solution and filtered on a vacuum through a Millipore AP20, 42 mm Prefilter. The OR of the filtrate was then determined. A control using distilled water with no added dextran was used.

Results:
OR before filtration=2.16
OR after filtration=2.15
OR Control 2=−0.04

Conclusion: The presence of Filter Cel E during the filtration has no significant effect on the dextran concentration but may release some laevorotatory products.

EXAMPLE 4

Calibration Curve Constructed in 15% Sucrose

This information will be incorporated into the software of the polarimeter so that the user need not perform any calculations and therefore reduces the chances of error.

Sucrose is known to mildly retard the rate of the reaction with dextran via non-competitive inhibition.

Method: A 15% solution of sucrose was made up in distilled water. Using this solution, an 8000 ppm solution of 188 kDa dextran was made and with these two solutions, the following dilutions carried out.

−1:2 gives 4000 ppm dextran
−1:4 gives 2000 ppm dextran
−1:10 gives 800 ppm dextran
−1:20 gives 400 ppm dextran
−1:40 gives 200 ppm dextran The OR of each solution was treasured on the polarimeter and then 19 ml aliquots of each measured out in triplicate.

The dextranase is diluted 1:5 and 1 ml added to each of the 19 ml dextran solutions just prior to injection into the polarimeter. The reaction was followed for 15 minutes and the readings recorded at 5 second intervals by a data collection programme.

Results are shown in Table 2 and FIG. 2:

Results:

TABLE 2

Shows the change in optical rotation due to hydrolysis of dextran by dextranase for different dextran concentrations.

| Dextran (ppm) after correction for moisture content | OR°Z in 15% sucrose (after correcting for 19:20 dilution) | Change in OR°Z due to enzymatic hydrolysis |
|---|---|---|
| 179.93 | 55.31 | 0.0875 |
| 359.86 | 55.49 | 0.1723 |
| 719.72 | 55.88 | 0.3153 |
| 1799.30 | 56.98 | 0.7015 |
| 3598.60 | 58.96 | 1.2995 |
| 7197.20 | 62.96 | 2.5093 |

FIG. 2. Graph showing the linear relationship between dextran concentration and change in optical rotation due to hydrolysis by dextranase.

The relationship shown in FIG. 2 may be curve fitted and incorporated into polarimeter software to allow automatic result readings.

EXAMPLE 5

Detecting Spiked Dextran in Cane Juice

Dextran free cane juice was obtained from Florida and spiked with commercial dextran to demonstrate that dextran could be detected and quantified in cane juice as effectively and accurately as in distilled water.

Method: Make up a 2000 ppm solution of dextran (71.4 kDa) in distilled water and measure the OR. Filter and collect at least 200 ml cane juice using celite purification with Filter Cel E and measure the OR. Accurately weigh 0.1 g. dextran into a 50 ml flask and fill to mark with cane juice and measure the OR.

Results are presented in FIG. 3, a graph showing the difference between the optical rotational values of the clean and spiked juice and then the actual data compared to the predicted data the latter of which arises from adding the data. of the reaction in water to that of the unspiked juice (after accounting for controls).

Conclusion: There are no interfering factors present in this juice sample as shown by the equal end test values of the predicted and actual data (FIG. 3). Another finding, which is apparent from this data (FIG. 3), is the retarding effect of the high sucrose concentration on the rate of the reaction.

What is claimed is:

1. A method for measuring a concentration of a material in a solution, the method comprising the steps of:
   (i) dividing the material in a solution into samples;
   (ii) measuring an optical rotation of a sample;
   (iii) treating the sample with a reactive agent that reacts with the material to alter the optical rotation of the sample;
   (iv) measuring the optical rotation of the sample after the treating with the reactive agent to ascertain a difference that said treating produces; and
   (v) calculating the concentration of the material by reference of said difference to a suitable standard.

2. The method according to claim 1, wherein the concentration of the material is measured in a sugar solution.

3. The method according to claim 1, wherein the material is optically active.

4. The method according to claim 3, wherein the material is dextran or raffinose.

5. The method according to claim 4, wherein the material is dextran and the reactive agent is dextranase.

6. The method according to claim 1, further comprising a step of treating the sample with a second reactive agent.

7. The method according to claim 1, wherein the reactive agent is provided on a solid support.

8. The method according to claim 1, wherein the sample is purified with diatomaceous earth having a median particle size of less than 19.3 microns prior to measuring the optical rotation.

9. The method according to claim 1, wherein the reactive agent is dextranase or α-galactosidase on a solid support.

10. A method for a polarimetric analysis of a sample of a solution at near IR wavelengths, the method comprising the steps of:
   i treating the sample with diatomaceous earth having a median particle size of less than 19.3 microns;
   ii measuring an optical rotation of the sample;
   iii treating the sample with a reactive agent that reacts with a material in the sample to alter the optical rotation of the sample;
   iv measuring the optical rotation of the sample after the treatment with the reactive agent; and
   v calculating a concentration of the material by reference to a suitable standard.

11. The method according to claim 10, wherein the diatomaceous earth is a fine grading of diatomaceous earth or a functional equivalent.

* * * * *